United States Patent
Nishida et al.

(10) Patent No.: US 10,457,913 B2
(45) Date of Patent: Oct. 29, 2019

(54) CORNEAL EPITHELIOID CELLS DERIVED FROM SURFACE ECTODERMAL CELLS

(71) Applicant: Osaka University, Suita-shi, Osaka (JP)

(72) Inventors: Kohji Nishida, Osaka (JP); Yuzuru Sasamoto, Osaka (JP); Ryuhei Hayashi, Osaka (JP)

(73) Assignee: Osaka University, Osaka (JP)

( * ) Notice: Subject to any disclaimer, the term of this patent is extended or adjusted under 35 U.S.C. 154(b) by 1 day.

(21) Appl. No.: 15/543,021

(22) PCT Filed: Jan. 12, 2016

(86) PCT No.: PCT/JP2016/050619
§ 371 (c)(1),
(2) Date: Jul. 12, 2017

(87) PCT Pub. No.: WO2016/114242
PCT Pub. Date: Jul. 21, 2016

(65) Prior Publication Data
US 2018/0148685 A1    May 31, 2018

(30) Foreign Application Priority Data

Jan. 13, 2015  (JP) ................................ 2015-004389

(51) Int. Cl.
*C12N 5/071*   (2010.01)
*C07K 14/47*   (2006.01)
*C12N 15/86*   (2006.01)

(52) U.S. Cl.
CPC ........ *C12N 5/0602* (2013.01); *C07K 14/4702* (2013.01); *C12N 15/86* (2013.01); *C12N 2501/60* (2013.01); *C12N 2501/603* (2013.01); *C12N 2501/604* (2013.01); *C12N 2506/097* (2013.01); *C12N 2740/15043* (2013.01)

(58) Field of Classification Search
CPC .... C12N 5/0602; C12N 14/4702; C12N 5/10; C12N 15/86; C12N 2501/60; C12N 2501/603; C12N 2501/604; C12N 2506/097; C12N 2740/15043
See application file for complete search history.

(56) References Cited

U.S. PATENT DOCUMENTS

| | | |
|---|---|---|
| 2005/0003532 A1 | 1/2005 | Nakamura et al. |
| 2008/0026030 A1 | 1/2008 | Kinoshita et al. |
| 2012/0142103 A1 | 6/2012 | Nishida et al. |
| 2013/0251692 A1 | 9/2013 | Itskovitz-Eldor et al. |

FOREIGN PATENT DOCUMENTS

| | | |
|---|---|---|
| JP | 2014-503200 A | 2/2014 |
| WO | WO 03/009783 A1 | 2/2003 |
| WO | WO 03/043542 A1 | 5/2003 |
| WO | WO 2006/003818 A1 | 1/2006 |

OTHER PUBLICATIONS

Tanifuji-Terai et al., IOVS, 47(2): 545-551, 2006.*
Prasad et al., Stem Cells and Development,26(3): 154-165, 2017.*
Saichanma et ali., Int. J. Ophthalmol. 5(2): 158-163, 2012.*
Yoshida et al., PLoS One, 6(12), e28856: 1-10, 2011.*
Kumagai et al., Cornea, 29(4): 432-438, 2010.*
Rostovskaya et al., Phil. Trans. R. Soc. B, 370: 1-11, 2015.*
Kobayashi et al., Molecular Vision, 15: 1589-1593, 2009.*
Japanese Office Action dated Jun. 5, 2018, in JP 2016-569347.
Ahmad et al., "Differentiation of Human Embryonic Stem Cells into Corneal Epithelial-Like Cells by In Vitro Replication of the Corneal Epithelial Stem Cell Niche," Stem Cells, 2007, 25:1145-1155.
International Search Report dated Apr. 5, 2016, in PCT/JP2016/050619.
Ieda et al., "Direct Reprogramming of Fibroblasts into Functional Cardiomyocytes by Defined Factors," Cell, Aug. 6, 2010, 142:375-386.
Nishida et al., "Corneal Reconstruction with Tissue-Engineered Cell Sheets Composed of Autologous Oral Mucosal Epithelium," The New England Journal of Medicine, Sep. 16, 2004, 351:1187-1196.
Shalom-Feuerstein et al., "Skin and corneal cellular therapy using embryonic stem cells: how far are we?", Expert Rev. Dermatol., 2008, 3(3):357-366.
Shiraishi et al., "Identification of the Cornea-Specific Keratin 12 Promoter by In Vivo Particle-Mediated Gene Transfer," Invest. Ophthalmol. Vis. Sci., Dec. 1998, 39(13):2554-2561.
Tsumaki, Noriyuki, "Direct induction of chondrogenic cells from mouse dermal fibroblast culture," Journal of Clinical and Experimental Medicine, Dec. 31, 2011, 239(14):1332-1337, with partial English translation.
Vierbuchen et al., "Direct conversion of fibroblasts to functional neurons by defined factors," Nature, Feb. 25, 2010, 463:1035-1041.
Yang et al., "Corneal epithelial-like transdifferentiation of hair follicle stem cells is mediated by pax6 and Beta-catenin/Lef-1," Cell Biology International, 2009, 33:861-866.
Yu et al., "Differentiation of mouse induced pluripotent stem cells into corneal epithelial-like cells," Cell Biology International, 2013, 37:87-94.
Supplementary European Search Report dated May 8, 2018, in EP 16737313.3.

\* cited by examiner

*Primary Examiner* — Thaian N Ton
(74) *Attorney, Agent, or Firm* — Foley & Lardner LLP

(57) ABSTRACT

The present invention relates to a method for inducing a keratin 12-positive corneal epithelioid cell from a surface ectoderm-derived cell. More specifically, the present invention relates to a method for inducing a keratin 12-positive corneal epithelioid cell, comprising introducing PAX6, KLF4, and OCT4 into a surface ectoderm-derived cell, such as an oral mucosal epithelial cell, and a corneal epithelioid cell induced by the method.

7 Claims, 9 Drawing Sheets

A

B

A

B

C

CORNEAL EPITHELIOID CELLS DERIVED FROM SURFACE ECTODERMAL CELLS

RELATED APPLICATIONS

This application is a National Stage application of PCT/JP2016/050619, filed Jan. 12, 2016, which claims priority to Japanese Patent Application No. 2015-004389, filed Jan. 13, 2015, the contents of which are incorporated herein by reference.

TECHNICAL FIELD

The present invention relates to a method for inducing a keratin 12-positive corneal epithelioid cell from a surface ectoderm-derived cell. More specifically, the present invention relates to a method for inducing a K12-positive corneal epithelioid cell, comprising introducing PAX6, KLF4, and OCT4 into a surface ectoderm-derived cell, such as an oral mucosal epithelial cell, and a corneal epithelioid cell induced by the method.

BACKGROUND ART

Corneal transplantation through eye donation is performed for intractable corneal epithelial disease; however, it has problems of absolute donor shortage and rejection reaction after transplantation. To solve these problems, a therapeutic method using patient's own oral mucosal epithelial cells has been developed. This method involves preparing a cultured corneal epithelioid cell sheet from oral mucosal epithelial cells and transplanting the sheet into the affected eye (Patent Literatures 1 to 3 and Non Patent Literature 1). However, this method has the following problem: the sheet using the oral mucosal epithelium is low in transparency and weak compared to that using the corneal epithelium since the mucosal epithelium does not differentiate into a complete corneal epithelium. Because of a difference in the ability to cause vascularization, the invasion of blood vessel may occur in the naturally blood-vessel-free cornea in some cases, after transplanting the oral mucosal epithelial sheet.

Meanwhile, the regenerative medicine research is underway which attempts to compensate damaged tissue/organ by inducing the differentiation of undifferentiated cells (stem cells). Embryonic stem cells (ES cells) can be differentiated into all cells other than those of the placenta, and thus attention has been given to their differentiation induction into each cell lineage and the identification of a factor determining their differentiation. However, the research and use of the stem cells have many limitations due to ethical problems and there is also a problem of rejection reaction. Thus, ES cells have not yet been clinically applied.

The regenerative medicine using artificial pluripotent stem cells, such as iPS cells, not only has no ethical problem but also can use patient-derived cells as a source to avoid the problem of rejection. However, some iPS cells remain as undifferentiated cells even after differentiation induction, and have a risk of tumorigenic transformation after transplanting. There is also the following problem: the establishment and differentiation induction of iPS cells takes several months or more.

On the other hand, methods are known for inducing nerve cells (Non Patent Literature 2) and myocardial cells (Non Patent Literature 3) from skin fibroblasts by direct reprogramming, in which desired somatic cells are directly induced without being via iPS cells. According to these methods, desired somatic cells can be simply obtained in a short period of time without the risk of tumorigenic transformation resulting from the remaining of undifferentiated cells.

CITATION LIST

Patent Literature

Patent Literature 1
  International Publication No. WO2003/009783
Patent Literature 2
  International Publication No. WO2003/043542
Patent Literature 3
  International Publication No. WO2006/003818

Non Patent Literature

Non Patent Literature 1
Nishida K. et al., N. Engl. J. Med., (2004) 351: 1187-96
Non Patent Literature 2
Vierbuchen T. et al., Nature, (2010) 463: 1035-1041
Non Patent Literature 3
Ieda M., Cell. (2010) 142 (3): 375-86.

SUMMARY OF INVENTION

Technical Problem

An object of the present invention is to induce a cell having functions close to those of a natural corneal epithelial cell by direct reprogramming not through the state of a pluripotent cell.

Solution to Problem

To solve the above problems, it has been found that in addition to transcription factors, PAX6 and KLF4, which are known to be expressed in corneal epithelium, OCT4 can be introduced into an oral mucosal epithelial cell, which is embryologically and functionally similar to a corneal epithelial cell, to induce a corneal epithelioid cell expressing keratin 12 specific to the corneal epithelium not through a state of a pluripotent cell.

Thus, the present invention provides the following (1) to (12):

(1) A method for producing a corneal epithelial cell, comprising introducing PAX6, KLF4, and OCT4 into a surface ectoderm-derived cell to induce a keratin 12-positive corneal epithelioid cell.

(2) The method according to (1) above, wherein the corneal epithelioid cell is induced not through a state of a pluripotent cell.

(3) The method according to (1) or (2) above, wherein the surface ectoderm-derived cell is an oral mucosal epithelial cell.

(4) The method according to any of (1) to (3) above, wherein the corneal epithelioid cell is further keratin 3-positive.

(5) The method according to (4) above, wherein two PAX6 isoforms, Pa and Pb, are both introduced.

(6) The method according to any of (1) to (5) above, wherein PAX6, KLF4, and OCT4 are introduced using one virus vector.

(7) A method for producing a corneal epithelioid cell sheet, comprising producing corneal epithelioid cells by the method according to any of (1) to (6) above and stratifying the cells.

(8) A keratin 12-positive corneal epithelioid cell directly induced from a surface ectoderm-derived cell.

(9) The corneal epithelioid cell according to (8) above, wherein the corneal epithelioid cell is further keratin 3-positive.

(10) The corneal epithelioid cell according to (8) or (9) above, wherein the surface ectoderm-derived cell is an oral mucosal epithelial cell.

(11) The corneal epithelioid cell according to (10), obtained by introducing PAX6, KLF4, and OCT4 into the surface ectoderm-derived cell.

(12) A corneal epithelioid cell sheet prepared by stratifying the cells according to any of (8) to (11) above.

Advantageous Effects of Invention

No expression of keratin 12 is observed for a conventional cultured oral mucosal epithelial cell sheet, which has been considered to be a cause of its insufficient transparency. According to the present invention, a cell positive for keratin 12 specific to corneal epithelium can be induced from an ectoderm-derived cell, such as an oral mucosal epithelial cell. In addition, the use of the keratin 12-positive cultured oral mucosal epithelial cell as a cell source enables the preparation of a corneal epithelioid cell sheet having properties close to the properties of an corneal epithelial cell compared to those of a conventional cultured oral mucosal epithelial sheet.

According to the method of the present invention, since a corneal epithelioid cell is directly induced from a somatic cell not through a state of a pluripotent cell, a desired cell can be simply obtained in a short period of time with a reduced risk of tumorigenic transformation compared to that for induction from a pluripotent stem cell. As a result, the method enables a clinically more favorable outcome to be obtained, and is also conducive to the improvement of patient's QOL.

DESCRIPTION OF EMBODIMENTS

1. Definition

Figure 1:
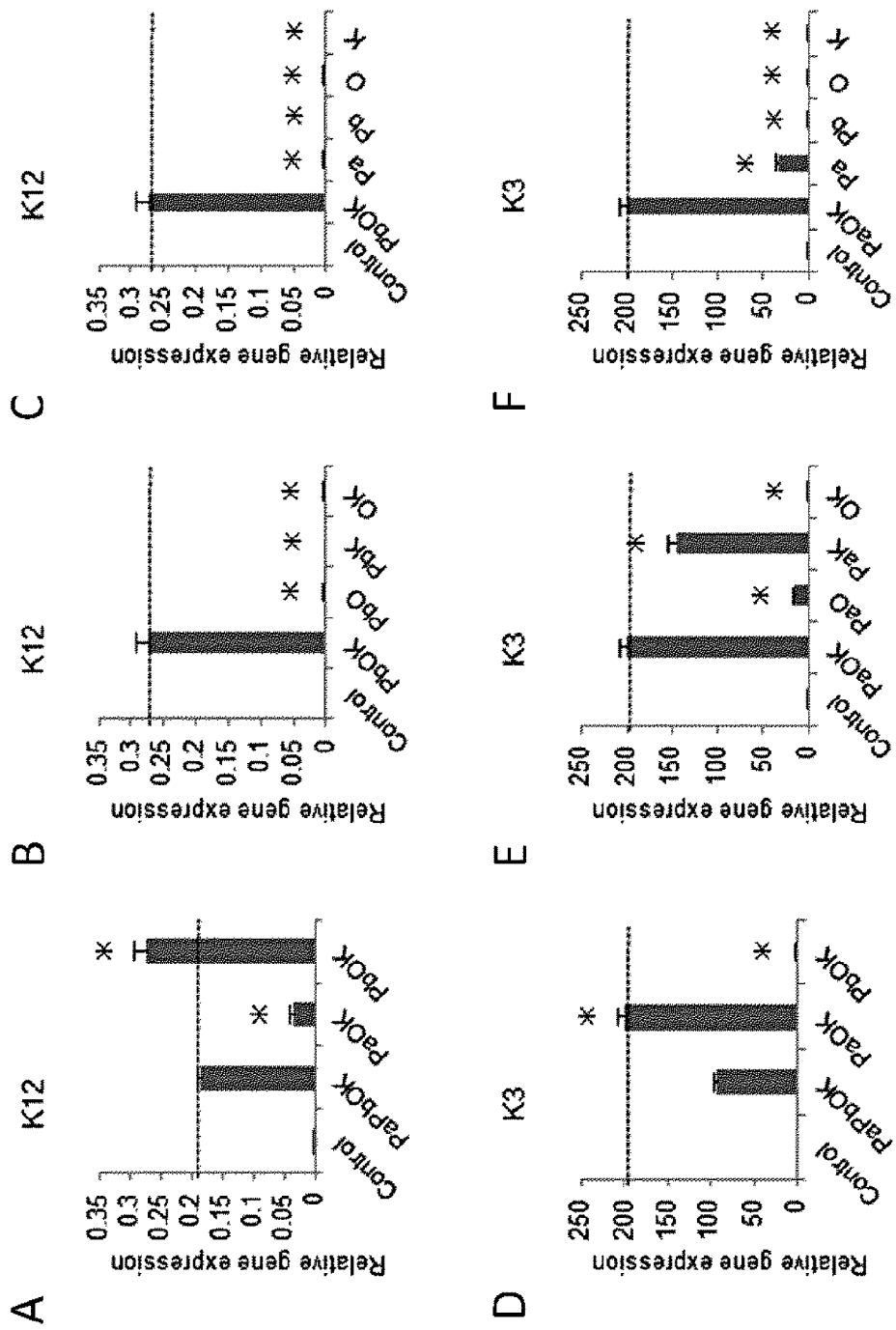
FIG. 1 is a series of graphs showing the results of confirming the expression of mRNA of K12 (A to C) and K3 (D to F) by real-time PCR. The remarkable expression of mRNA could be induced using the combination of PbOK for K12 and using the combination of PaOK or PaK, or Pa for K3.

Surface Ectoderm-Derived Cell:

The human embryo forms 3 germ layers, i.e. endoderm, mesoderm, and ectoderm, during the stage of development. The endoderm becomes the mucosal epithelium of stomach and small bowel, liver, pancreas, or the like; the mesoderm becomes muscle, bone, blood vessel, blood, subcutaneous tissue, heart, kidney, or the like; and the ectoderm forms nerve, eye (corneal epithelium), epiderm, or the like. The ectoderm is further divided into the neuroectoderm, which becomes the brain or nerve tissue, and the surface ectoderm, which mainly becomes epithelial tissue on the skin surface, and the latter is called "surface ectoderm-derived cells".

Examples of "surface ectoderm-derived cells" include stratified epithelial cells covering body surfaces, such as epiderm, oral mucosal epithelium, and corneal epithelium. Particularly, the oral mucosal epithelium is functionally close to the corneal epithelium and easy to obtain and thus is preferable as a source for inducing corneal epithelioid cells.

PAX6:

"PAX6 (paired box protein)" is a transcription factor expressed during embryonic development and also called an iridia type II protein (AN2) or oculorhombin. PAX6 is an important regulatory gene in the development of the eyes and brain, and the protein encoded by PAX6 can bind to DNA and has two different binding sites functioning as regulator for gene transcription. The mutation of PAX6 is known to cause various abnormalities of the eye. Two isoforms, Pa and Pb, are present in "PAX6". One containing no 5a sequence in the PAIRED domain among the DNA-binding sites is Pa and one containing it is Pb.

KLF4:

"KLF4 (Kruppel-like factor 4" is a member of the KLF transcription factor family and controls proliferation, differentiation, apoptosis, and somatic cell reprogramming.

OCT4:

"OCT4 (octamer-binding transcription factor 4)" is a transcription factor having the POU (Pit-Oct-Unc) domain and plays an important role in early embryonic development and the maintenance of ES cell pluripotency. OCT4 changes the epigenomic state and is closely involved in the self-replication of an undifferentiated embryonic stem cell, and thus is utilized as an undifferentiation marker (a pluripotency marker). It is also used as a marker for the canceration of a germ cell.

Corneal Epithelioid Cell:

Cornea has the 3-layer structure of a corneal epithelial layer, a corneal stromal layer, and a corneal endothelial layer in order from the surface. Corneal epithelial cells are cells constituting the outermost layer of the cornea and consist of 4 to 5 corneal epithelial cell layers. The corneal epithelial cell is derived from the epidermal ectoderm while the corneal stroma and endothelium are derived from the neural crest; there are considered to be separate stem cells therefor. The "corneal epithelioid cell" according to the present invention is a cell having functions and properties similar to those of the corneal epithelial cell, and is characterized by the expression of keratin 12 as a corneal epithelial differentiation marker.

Corneal Epithelial Cell-Specific Marker:

Keratin 12 (cytokeratin 12: K12) and keratin 3 (cytokeratin 3: K3) are each a corneal epithelial cell-specific marker.

Pluripotency Marker:

According to the present invention, it is a cellular gene/protein providing an index of the pluripotency of a human cell. Examples of the pluripotency (stem cell) marker can include OCT4 (shown above), NANOG, TRA-1-60, and SSEA-4.

NANOG:

NANOG is a transcriptional regulatory factor involved in the proliferation and self-replication of an inner cell mass and ES cells. It suppresses the differentiation of ES cells into extraembryonic endoderm and trophectoderm and maintains their pluripotency. NANOG is considered to prevent endoderm differentiation of ES cells by the BMP signal by acting on SMAD1 and inhibiting the binding of a coactivator activating the transcription of SMAD1.

TRA-1-60:

An anti-TRA-1-60 antibody recognizes an antigen expressed on the surface of a human EC cell, an EG cell, an ES cell, or an iPS cell.

SSEA-4:

SSEA-4 (stage specific embryonic antigen 4) is a kind of glycosphingolipid localized on the cell surface. In the human, the expression of SSEA-4 is observed on an EC cell, an EG cell, and an ES cell; however, its expression is reduced with differentiation and the expression of SSEA-1 is increased instead. Thus, SSEA-4 is used as a human pluripotency (stem cell) marker.

2. Induction of Corneal Epithelioid Cell

According to the present invention, the keratin 12 (K12)-positive corneal epithelioid cell is induced by introducing PAX6, OCT4, and KLF4 into a surface ectoderm-derived cell.

The method for gene introduction is not particularly limited and can be carried out using a known vector. The vector is not particularly limited provided that it enables the introduction of the genes into mammalian cells. For example, viral vectors can be used, such as an adenoviral vector, an adeno-associated viral vector, a retroviral vector, a lentiviral vector, and a Sendai virus. Among these, the adenoviral vector is high in toxicity though it can be abundantly expressed; the retroviral vector is unsuited for nondividing cells though it can be expected to be stably expressed over a long period of time; and the adeno-associated viral vector has a disadvantage that a large gene cannot be incorporated thereinto. In contrast, the lentiviral vector has no such problems and can be expected to be stably expressed over a long period of time.

PAX6, OCT4, and KLF4 may be introduced using separate vectors or using one vector. As demonstrated in Examples to be described later, even the in-series arrangement and introduction of the genes into one vector results in the independent expression of the proteins, and enables a K12-positive corneal epithelioid cell to be obtained as in the case of separate introduction.

According to the above method, the surface ectoderm-derived cell is directly induced into the corneal epithelioid cell not through a pluripotent state. Therefore, there is little risk of tumorigenic transformation attributed to that undifferentiated cells remain as in the case of induction from pluripotent stem cells, enabling desired corneal epithelioid cells to be simply obtained in a short time.

Examples of the surface ectoderm-derived cell include epidermal, oral mucosal epithelial, and corneal epithelioid cells; however, preferred is an oral mucosal epithelial cell similar in terms of function, more preferably, an oral mucosal epithelial cell of a patient per se into which the corneal epithelioid cell obtained is transplanted.

The culture medium for the cells is not particularly limited provided that it is a medium usable for the culture of epithelial cells. A commercially available medium for epithelial cells may be used, or a medium may be used which is prepared by adding various nutrient sources necessary for the maintenance and proliferation of cells and components necessary for differentiation induction to a basal medium. As the basal medium, any medium usable for animal cell culture may be used, such as DMEM medium, Keratinocyte-SFM medium, BME medium, BGJb medium, CMRL 1066 medium, Glasgow MEM medium, Improved MEM Zinc Option medium, IMDM medium, Medium 199 medium, Eagle MEM medium, αMEM medium, Dulbecco MEM medium, Ham's medium, RPMI 1640 medium, Fischer's medium, McCoy's medium, Williams E medium, or a mixed medium thereof.

Examples of the nutrient source can include: carbon sources, such as glycerol, glucose, fructose, sucrose, lactose, honey, starch, and dextrin; carbohydrates, such as fatty acid, oil and fat, lecithin, and alcohols; nitrogen sources, such as ammonium sulfate, ammonium nitrate, ammonium chloride, urea, and sodium nitrate; inorganic salts, such as common salt, potassium salt, phosphate, magnesium salt, calcium salt, iron salt, and manganese salt; monopotassium phosphate, dipotassium phosphate, magnesium sulfate, sodium chloride, ferrous sulfate, sodium molybdate, sodium tungstate, and manganese sulfate; vitamins; and amino acids.

In addition, as needed, amino acid reducing agents, such as retinoic acid, pyruvic acid, pyruvic acid, and β-mercaptoethanol, and serum or serum substitutes can be listed. Examples of the serum substitute include albumin (e.g., lipid-rich albumin), transferrin, fatty acid, insulin, collagen precursors, trace elements, β-mercaptoethanol or 3'-thiolglycerol, growth factors (e.g., epidermal growth factor (EGF) and keratinocyte growth factor (KGF)), commercial Knockout Serum Replacement (KSR), bovine pituitary extracts (BPE), Chemically-defined Lipid concentrated (from Gibco Co., Ltd.), Glutamax (from Gibco Co., Ltd.), B27 supplement (from Gibco Co., Ltd.), and Y-27632 (Wako Pure Chemical Industries Ltd.).

The pH of a medium obtained by blending these components is in the range of 5.5 to 9.0, preferably 6.0 to 8.0, more preferably 6.5 to 7.5.

Culture is carried out under conditions of 36° C. to 38° C., preferably 36.5° C. to 37.5° C., 1% to 25% $O_2$, and 1% to 15% $CO_2$.

The corneal epithelioid cell preferably expresses keratin 3 (K3) in addition to K12. The expression of K12 and K3 at a gene level can easily be confirmed by real-time PCR, and the expression thereof at a protein level can easily be confirmed by immunostaining using antibodies specific to K12 and K3.

PAX6 has two isoforms, Pa and Pb; it is probable that Pb mainly controls the expression of K12 and that Pa mainly controls the expression of K3. According to the present invention, the introduction of both Pa and Pb provides both K12 and K3.

3. Corneal Epithelioid Cell Induced from Surface Ectodermal Cell

The present invention also provides a K12-positive corneal epithelioid cell induced from a surface ectoderm-derived cell. The cell is preferably further K3-positive.

K12 and K3 are each a corneal epithelial cell-specific marker, and the cell expressing K12 and/or K3 have the same functions and properties as those of a natural corneal epithelial cell. Therefore, the corneal epithelioid cell of the present invention can be used as a cell preparation for research or regenerative medicine.

The cell preparation may contain a scaffolding or component for assisting cell maintenance/proliferation or administration to an affected part and another pharmaceutically acceptable carrier. Examples of the component necessary for the maintenance/proliferation of cells include medium components, such as carbon sources, nitrogen sources, vitamins, minerals, salts, and various cytokines, or extracellular matrix preparations, such as Matrigel™.

Examples of the scaffolding and component for assisting administration to an affected part include biodegradable polymers, for example, collagen, polylactic acid, hyaluronic acid, cellulose, and their derivatives, and complexes consisting of 2 or more thereof, and aqueous solutions for injection, for example, physiological buffers, such as saline, medium, and PBS, and isotonic solutions containing glucose and other auxiliary substances (e.g., D-sorbitol, D-mannose, D-mannitol, and sodium chloride); a suitable solubilizer, for example, an alcohol, such as ethanol or polyalcohol (e.g., propylene glycol or polyethylene glycol) or a non-ionic surfactant, such as polysorbate 80 or HCO-50, may be used in combination therewith.

In addition, a pharmaceutically acceptable organic solvent, polyvinyl alcohol, polyvinylpyrrolidone, carboxyvinyl polymer, carboxymethylcellulose sodium, sodium polyacrylate, alginate sodium, water-soluble dextran, carboxymethyl starch sodium, pectin, methylcellulose, ethylcellulose, xanthan gum, gum Arabic, casein, agar, polyethylene glycol, diglycerine, glycerin, propylene glycol, vaseline, paraffin, stearyl alcohol, stearic acid, mannitol, sorbitol, or lactose, and a pharmaceutically acceptable surfactant, buffer, emulsifier, suspension agent, soothing agent, stabilizer, or the like may be contained, if necessary.

A practical additive is selected depending on a dosage form of therapeutic agents according to the present invention, from among the above substances alone or in proper combination; however, it is not intended to be limited thereto. For example, in the case of use as an injectable preparation, the preparation may be one obtained by dissolving a purified antibody in a solvent (e.g., saline, buffer, or a glycose solution) and adding an adsorption-preventing agent (e.g., Tween 80, Tween 20, or gelatin) thereto.

Examples of a disease capable of being a target for the cell preparation of the present invention include Stevens-Johnson syndrome, ocular pemphigoid, thermal/chemical injury, aniridia, corneal peripheral ulcer, limbal tumor, and gelatinous drop-like corneal dystrophy.

4. Corneal Epithelioid Cell Sheet

A corneal epithelioid cell sheet can be prepared by stratifying the K12-positive corneal epithelioid cells obtained by the method of present invention. The present invention also provides such a corneal epithelioid cell sheet and a method for the production thereof.

The stratification of cells can be carried out according to the previous reports by the inventors (e.g., International Publication No. WO 2004/069295, Japanese Patent Laid-Open No. 2005-130838, and Nishida k et al., N. Engl. J. Med. (2004) 351: 1187-96). For example, the corneal epithelioid cells induced by the method of the present invention are cultured on a porous membrane while supplying the medium from the underlayer via the porous membrane, and thus epithelial cells can be stratified to prepare a cultured epithelial cell sheet (Japanese Patent Laid-Open No. 2005-130838).

The resultant cell sheet is excellent in transparency and mechanical strength and has the same properties and functions as those of natural corneal epithelial cells. Therefore, the sheet is more suitable for clinical application.

EXAMPLES

Example 1: Induction of Corneal Epithelioid Cell from Oral Mucosal Epithelial Cell 1. Material/Method:
(Cell)
Immortalized human oral epithelial cells (OKF6/TERT-1 cells) were used.
(Medium/Culture Condition)
Cells were cultured under conditions of 5% $CO_2$ and 37° C. in Keratinocyte-SFM to which 25 μg/mL bovine pituitary extract (BPE), 0.2 ng/ml epidermal growth factor (EGF), and 0.3 mM $CaCl_2$ were added.
(Vector Construction)
An all-in-one vector in which PAX6 isoforms, Pa and Pb, their mutants, and PAX6-OCT4-KLF4 were linked using 2A was inserted into pLenti7.3/V5-DEST vector (Life Technologies). OCT4 and KLF4 were inserted into CSV-CMV-MCS-IRES2-Venus plasmid (RIKEN BIO Resource Center).

The PAX6 isoforms were hereinafter sometimes referred to as Pa and Pb; KLF4, as K; and OCT4, as O.
(Transduction)
The pLenti7.3-related vector was introduced into 293FT cells using ViraPower Lentiviral Expression System (Life Technologies) to produce a lentivirus. The CSV-CMV-MCS-IRES2-Venus plasmid-related vector was introduced into 293T cells using FuGene HD (Roche) together with pCMV-VZV-G-RSV-Rev and pCAG-HIV-gp (RIKEN Bio Resource Center) to produce a lentivirus.

These lentiviruses were each caused to infect the cells seeded at $1.875 \times 10^4$ cells/48-well plate a day ahead (and polybrene was also added); the following day, the medium was replaced; and culture was further carried out for 2 days.

(PCR)

RNA was extracted with RNeasyPlus Micro Kit and converted to cDNA using SuperScript III First-Strand Synthesis System. cDNA was quantified by Taqman Gene Expression Assay.

(Immunostaining)

The cultured cells fixed with 100% cold methanol or 4% paraformaldehyde were blocked and permeabilized using 5% normal donkey serum at ordinary temperature for 1 hour. After that, an anti-sheep K12 antibody, an anti-mouse K3/76 antibody, an anti-rabbit NANOG antibody, an anti-mouse SSEA4 antibody, or anti-mouse TRA-1-60 antibody was added thereto, which was then incubated at 4° C. overnight. In addition, the resultant was incubated together with a mouse, rabbit, or sheep secondary antibody. Finally, Hoechst 33342 was added, and images were obtained.

2. Result (1) Expression of Cornea-Specific Marker

As a result of real-time PCR, the expression of mRNA could be efficiently induced by the combination of PbOK for K12 and by the combination of PaOK or PaK, or Pa for K3 (FIG. 1).

Figure 2:
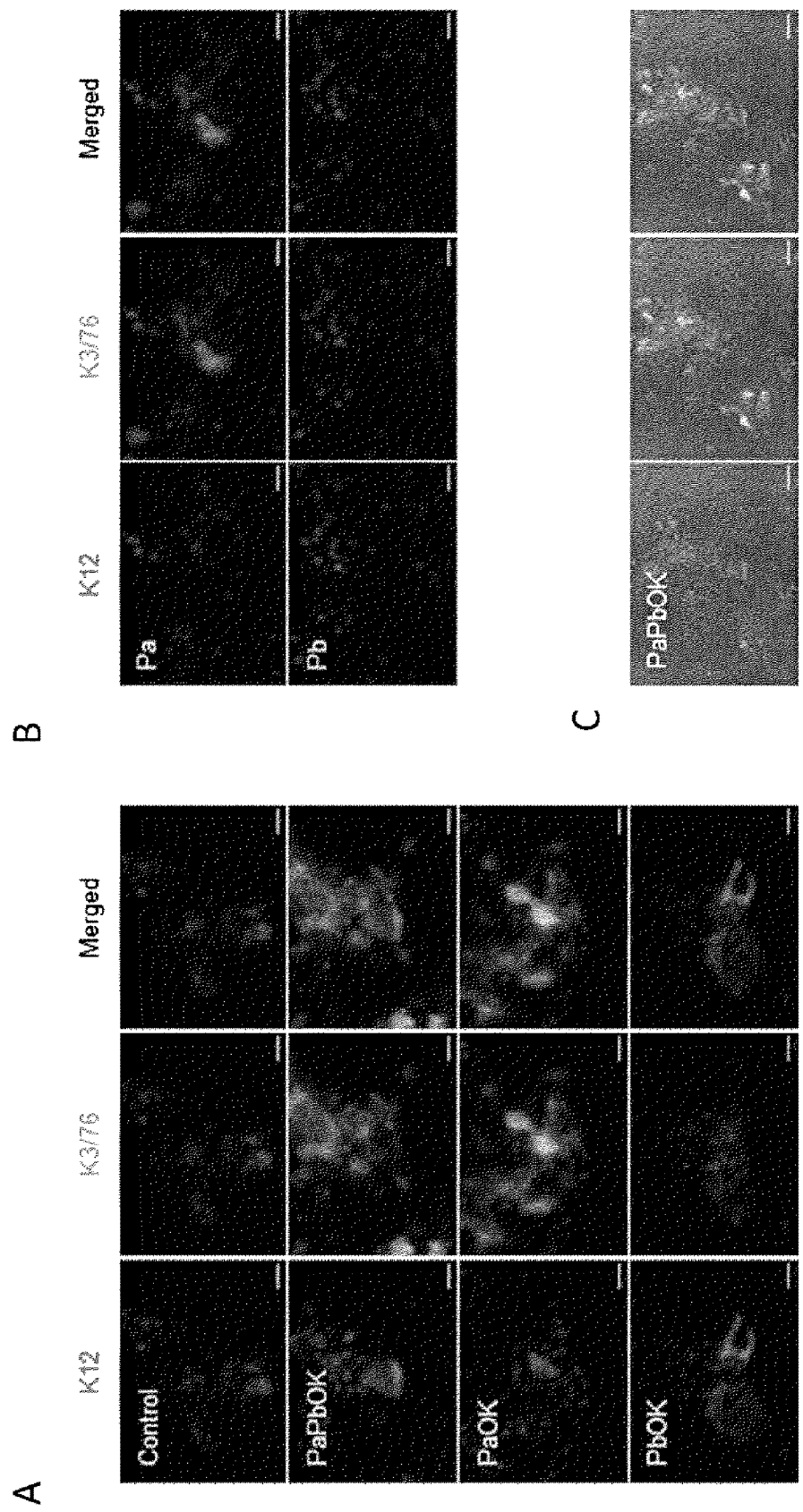
FIG. 2 is a series of photographs showing the results of confirming the expression of K12 and K3 at a protein level by immunostaining. Similar to the results of real-time PCR, remarkable expression was confirmed using the combination of PbOK for K12 and K3 and using the combination of PaOK, or Pa for K3.

As a result of immunostaining, similar to the expression of mRNA, the expression of K12 and K3 at a protein level was confirmed by the combination of PbOK for K12 and by the combination of PaOK, or Pa for K3 (FIG. 2).

(2) Expression of Pluripotency Marker

Figure 3:
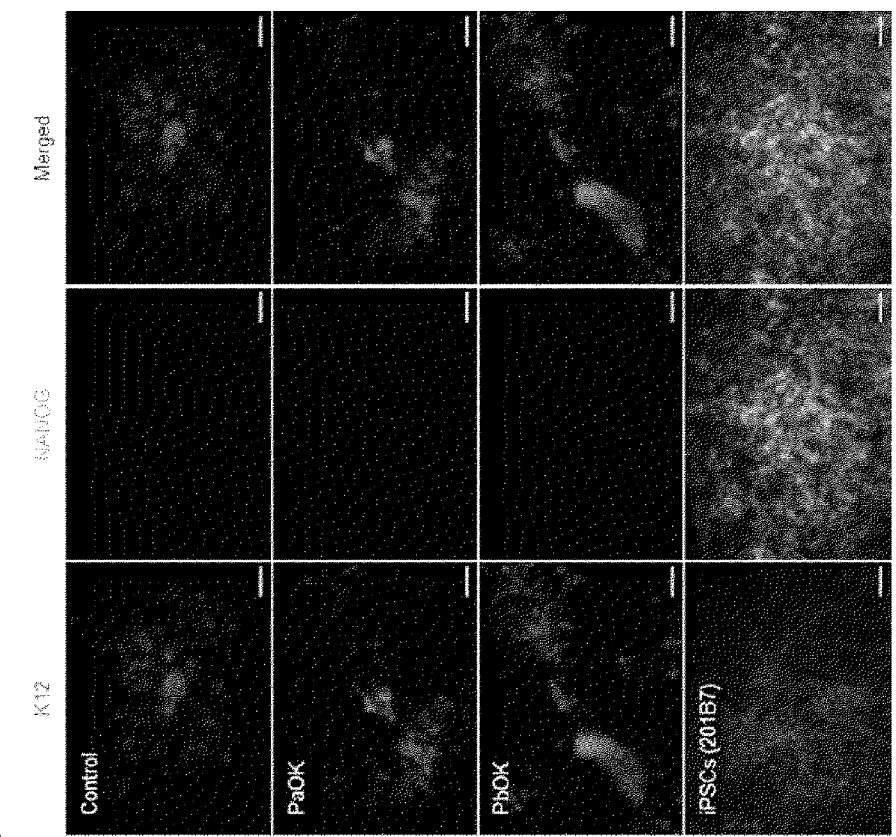
FIG. 3 is a pair of drawings showing the results of confirming the expression of NANOG as a pluripotency marker by real-time PCR and immunostaining. A slight increase in mRNA was observed at a single cell level, and no expression of NANOG was seen at a protein level although there is a possibility of partial reprogramming.
Figure 3:

When the expression of NANOG as a pluripotency marker was evaluated by real-time PCR and immunostaining, a slight increase in mRNA was observed at a single cell level, showing a possibility of partial reprogramming, however, the expression of NANOG was not observed at a protein level (FIG. 3).

Figure 4:
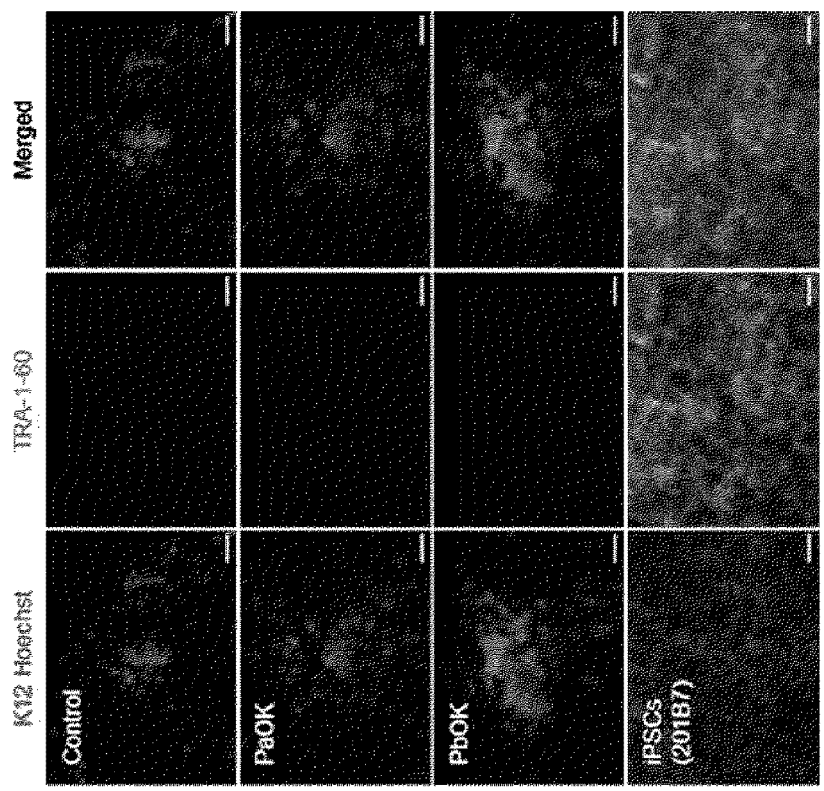
FIG. 4 is a series of photographs showing the results of confirming the expression of SSEA4 and TRA-1-60 as pluripotency markers by real-time PCR and immunostaining. No expression of SSEA4 and TRA-1-60 was observed in each cell.
Figure 4:
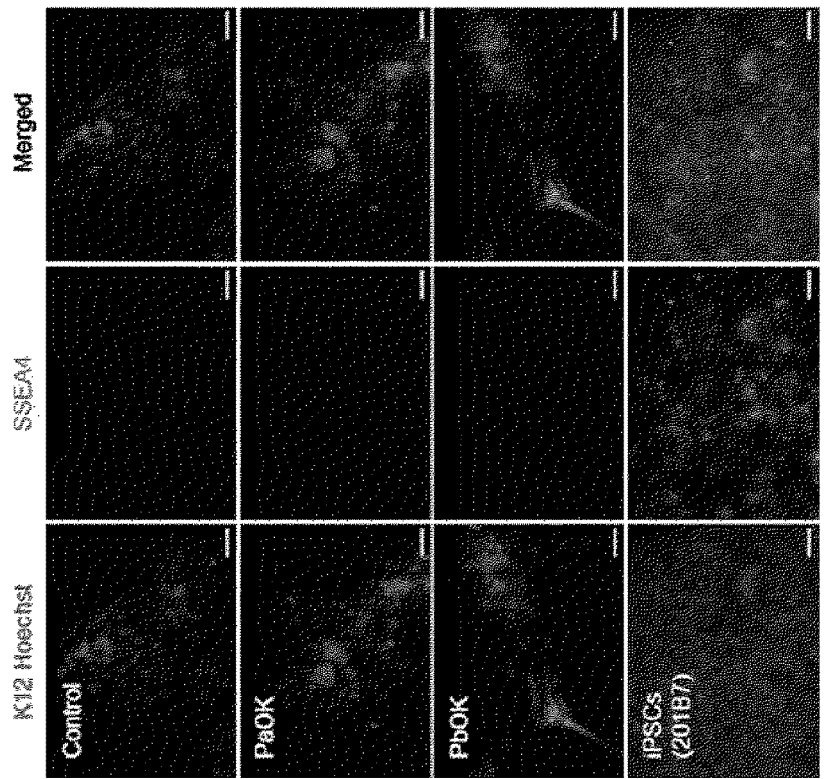

When the expression of SSEA4 and TRA-1-60 as pluripotency markers was evaluated by immunostaining, no expression thereof was observed (FIG. 4).

The above results confirmed that the expression of K3 and K12 was not induced through the state of pluripotent stem cells.

Example 2: Introduction of Genes into Various Cells

1. Material/Method (Cell Line)

Surface ectodermal cell: OKF6/TERT-1, OKF6/TERT-2, N/TERT-1, N/TERT-2, HOK

Neuroectoderm: ARPE-19, SH-SY5Y

Neural crest: HCEC

Mesoderm: HUVEC, NHDF-Ad, 293T

Endoderm: MKN1, HepG2 iPS cell: 201B7

PAX6 (Pa, Pb), KLF4, and OCT4 were introduced in various combinations into each of the above cell lines as in Example 1, and the expression of K12 and K3 on the resultant cells was confirmed by real-time PCR.

2. Result

Figure 5:
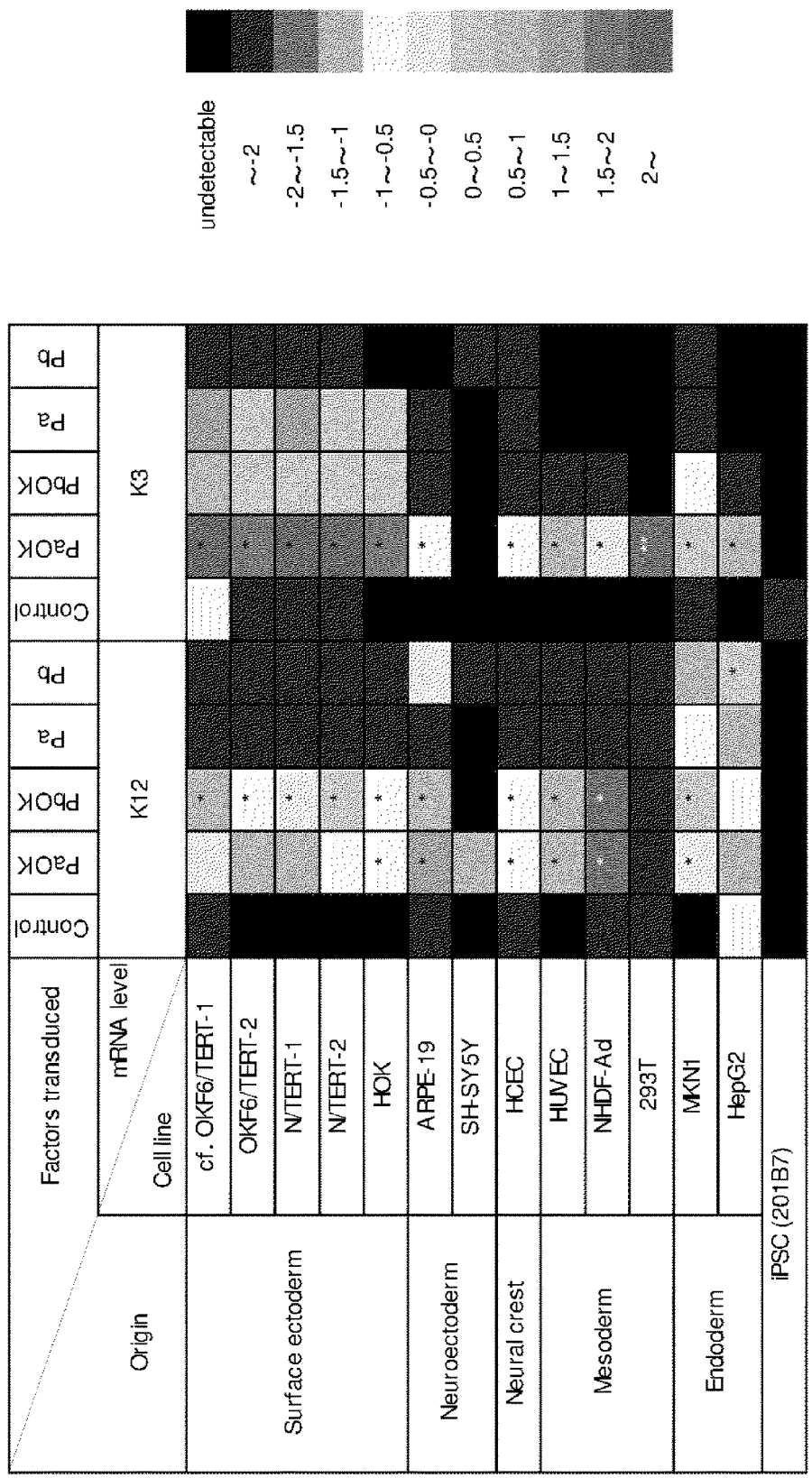
FIG. 5 is a table showing the results of confirming the expression of K12 and K3 by real-time PCR in various cells into which Pa, Pb, PaOK, or PbOK was introduced.

The results are collectively shown in FIG. 5. K12/K3 could be efficiently induced mainly on surface ectoderm-derived cells, but were little induced on endoderm- and mesoderm-derived cells and iPS cells. The induction efficiency was high in the surface ectoderm-derived cells having the same developmental origin as corneal epithelium.

Example 3: Introduction of Gene Using All-in-One Vector

1. Method

Using an all-in-one vector, 3 genes (PAX6, OCT4, and KLF4) were liked in the combination of PaOK or PbOK to a lentivirus vector through 2A sequences to prepare each of 2 types of vectors. The vector was transduced into oral mucosal epithelial cells in the same way as in Example 1, and the expression of mRNAs and proteins was evaluated by electrophoresis, real-time PCR, and immunostaining.

2. Result

Figure 6:
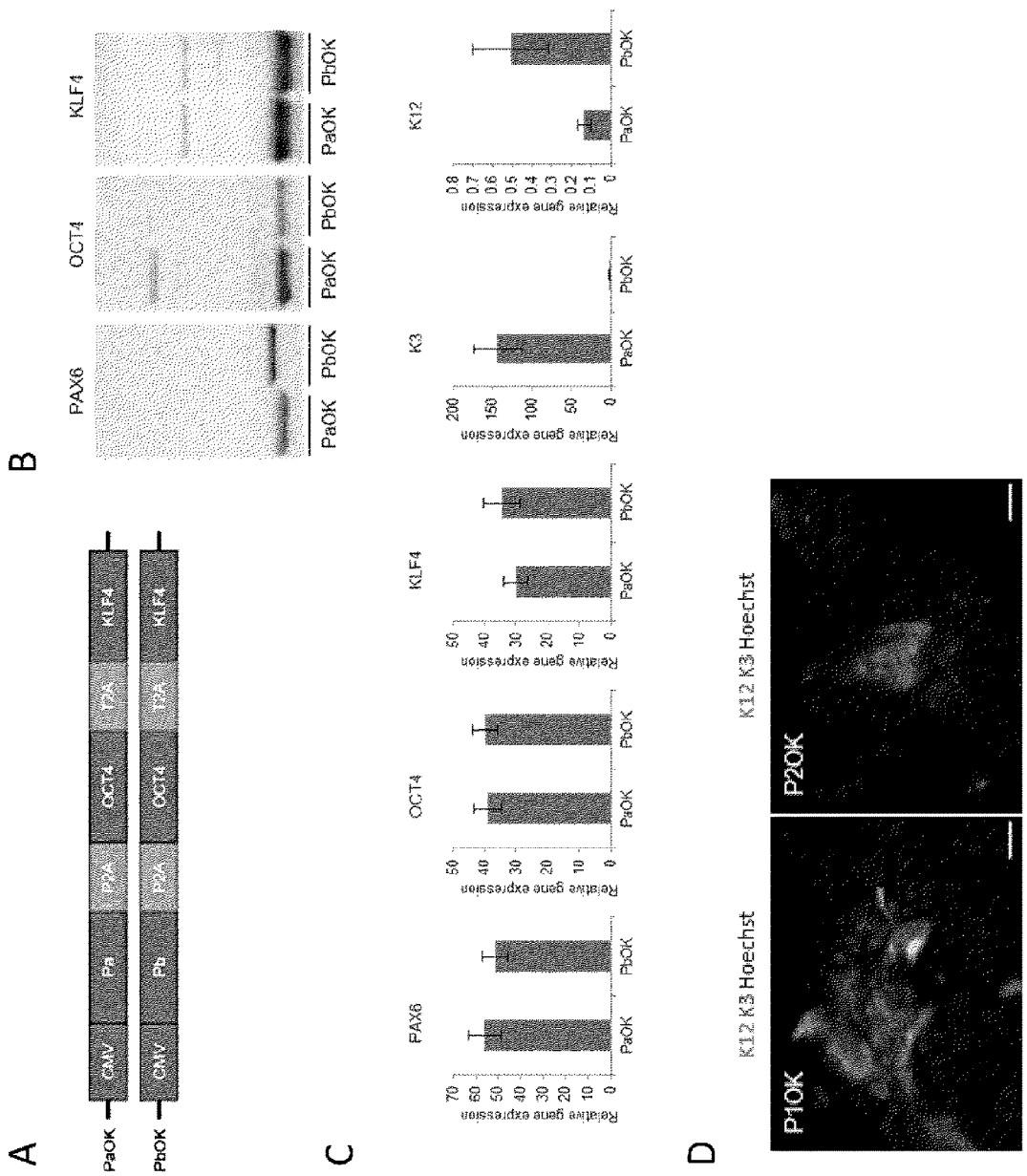
FIG. 6 is a series of drawings showing the results of mounting 3 genes (PAX6, OCT4, and KLF4) in one lentiviral vector (all-in-one vector), and introducing the vector into 293T cells, from which it was confirmed that most of the proteins were independently expressed. The expression of the mRNAs and the proteins is shown in the case of introduction into oral mucosal epithelial cells. It was confirmed that the use of the all-in-one vector provides the sufficient expression of PAX6, OCT4, and KLF4, and that thereby K12 and K3 can be induced.

As a result of electrophoresis, the proteins were confirmed to be expressed separated from one another. The results of real-time PCR and immunostaining confirmed that the use of the all-in-one vector provided the sufficient expression of PAX6, OCT4, and KLF4 and thereby enabled the induction of K12 and K3 (FIG. 6).

Example 4: Control of Expression of K12 and K3

Figure 7:
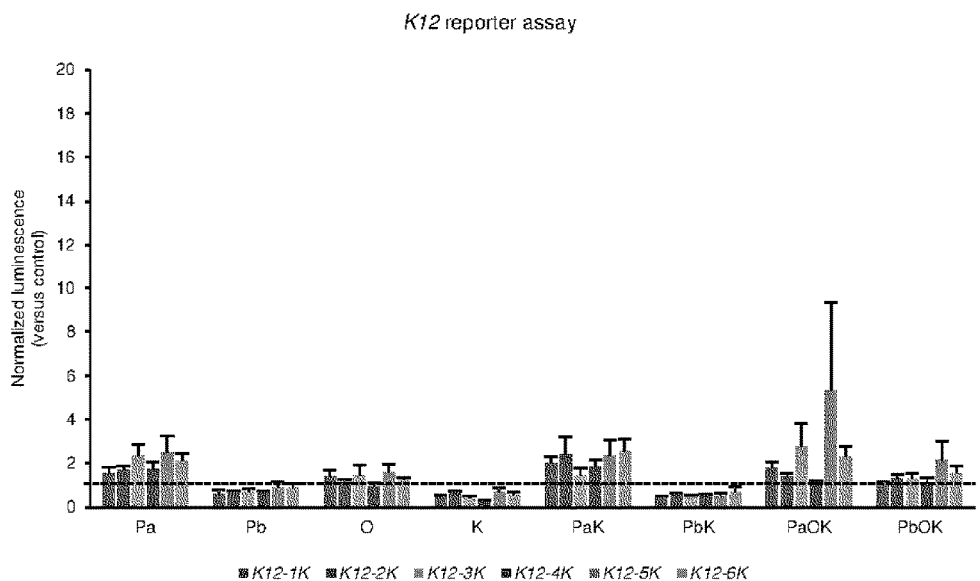
FIG. 7 is a pair of graphs showing the results of luciferase reporter assay of 1K to 6K upstream of K12 (A) or K3 (B) (from left in each graph, 1k, 2k, 3k, 4k, 5k, 6k).
Figure 7:
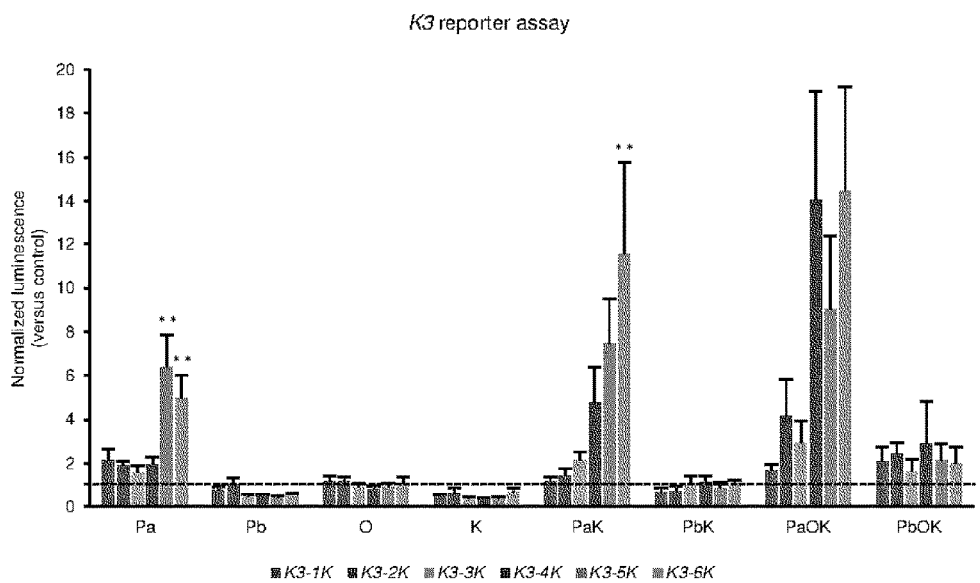

Six reporters in which secretory luciferase was bound to 1K to 6K sequences upstream of K12 or K3 were prepared, and various combinations of PaPbOK were each transduced together with each reporter into oral epithelial cells. As a result, Pa was confirmed to directly control expression upstream of K3 (FIG. 7).

Figure 8:
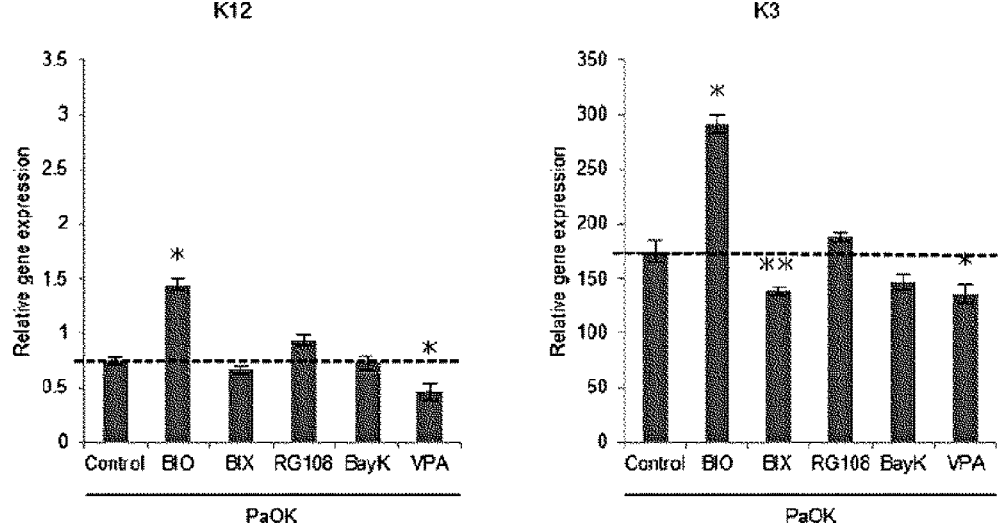
FIG. 8 is a series of graphs showing the results of the expression analysis of K12 (A) and K3 (B) after adding any of various small molecules (from left in each graph, control, BIO, BIX, RG108, BayK, and VPA) known to increase the efficiency of iPS establishment and be involved in its maintenance.
Figure 8:
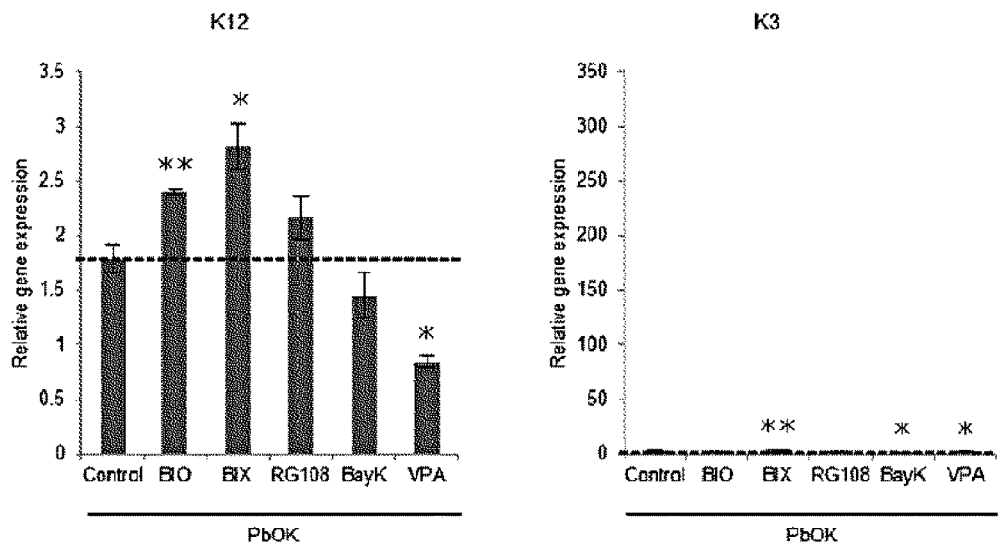

Small molecules involved in the establishment efficiency and maintenance of iPS cells were each added, and the expression of K12 and K3 was confirmed by real-time PCR. The added molecules were BIO involved in Wnt signaling, BIX involved in epigenomic modification, a DNA methyltransferase inhibitor RG108, a calcium channel agonist BayK, and valproic acid (VPA) as a histone deacetylase (HDAC) inhibitor. As a result, the addition of BIO or BIX was confirmed to increase the expression of K12 or K3 (FIG. 8). This showed that epigenomic modification by OCT4 or the small molecule (BIX) increased the efficiency of induction of K12 and Wnt signaling modification by BIO increased the efficiency of induction of K12 and K3.

Figure 9:
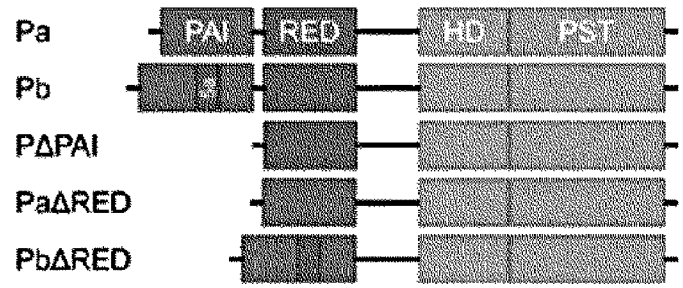
FIG. 9 is a series of drawings showing the results of the expression analysis of K12 (B) and K3 (C) by real-time PCR in cells obtained by deleting various combinations of the 2 DNA-binding domains (PAI and RED) of PAX6 and infecting with the resultant in combination with OCT4 and KLF4.
Figure 9:
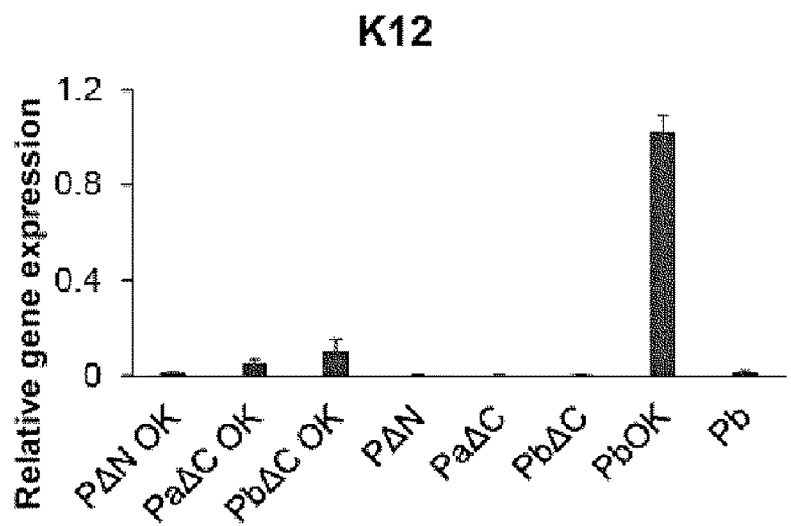
Figure 9:
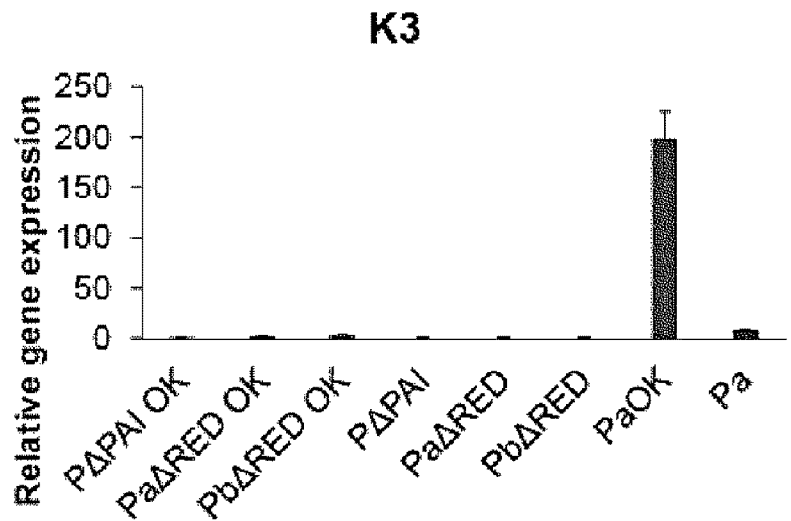

Oral mucosal epithelial cells were subjected to infection by combining the use of OCT4 and KLF4 with various combinations of deletions of the 2 DNA-binding domains (PAI and RED) of PAX6; as a result, the deletion of PAI and RED reduced the expression of both K12 and K3 (FIG. 9). This showed that both PAI and RED were necessary for the induction of K12/K3.

INDUSTRIAL APPLICABILITY

According to the present invention, keratin 12-positive cells close to natural corneal epithelial cells can be induced from surface ectoderm-derived cells, such as oral mucosal epithelial cells. The method of the present invention enables desired cells to be simply obtained in a short period of time with a reduced risk of tumorigenic transformation compared to that for induction from pluripotent stem cells. The cell sheet obtained by stratifying these cells is excellent in transparency and mechanical strength and thus is useful for the treatment of corneal epithelial diseases, such as cornea transplantation.

All publications, patents, and patent applications cited in this application are intended to be incorporated herein by reference in their entirety.

The invention claimed is:

1. An in vitro or ex vivo method for producing a keratin-12 positive human corneal epithelioid cell, comprising:
    introducing a lentiviral vector comprising nucleic acids encoding PAX6, KLF4, and OCT4 into a human epithelial cell, wherein expression of the lentiviral vector induces the production of a keratin 12-positive human corneal epithelioid cell.

2. The method according to claim 1, wherein the human corneal epithelioid cell is induced not through a state of a pluripotent cell.

3. The method according to claim 1, wherein the human epithelial cell is an oral mucosal epithelial cell.

4. A method for producing a human corneal epithelioid cell sheet, comprising producing human corneal epithelioid cells by the method according to claim 1 and stratifying the cells.

5. The method according to claim 1, wherein the lentiviral vector further comprises nucleic acids encoding two PAX6 isoforms, Pa and Pb.

6. The method according to claim 5, wherein the corneal epithelioid cell is further keratin 3-positive.

7. The method according to claim 1, the human epithelial cell is selected from the group consisting of epidermal cell, oral mucosal epithelial cell, and corneal epithelial cell.

* * * * *